United States Patent [19]

Keil

[11] 4,268,499

[45] May 19, 1981

[54] ANTIPERSPIRANT EMULSION COMPOSITIONS

[75] Inventor: Joseph W. Keil, Midland, Mich.

[73] Assignee: Dow Corning Corporation, Midland, Mich.

[21] Appl. No.: 46,590

[22] Filed: Jun. 7, 1979

[51] Int. Cl.³ .................. A61K 7/38; A61K 31/695
[52] U.S. Cl. .......................... 424/68; 424/47; 424/65; 424/66; 424/67; 424/168; 424/184
[58] Field of Search .................. 424/68, 184

[56] References Cited

U.S. PATENT DOCUMENTS

| Re. 29,814 | 10/1978 | Snyder | 424/184 |
|---|---|---|---|
| 3,406,238 | 10/1968 | Freyermuth et al. | 424/70 |
| 3,697,644 | 10/1972 | Laiderman | 424/362 |
| 3,836,647 | 9/1974 | Lange | 424/184 |
| 4,052,331 | 10/1977 | Dumoulin | 424/184 |
| 4,110,428 | 8/1978 | Kuhn et al. | 424/68 |
| 4,122,029 | 10/1978 | Gee et al. | 252/358 |
| 4,151,304 | 4/1979 | Evans | 424/362 |

FOREIGN PATENT DOCUMENTS

| 2057957 | 5/1971 | Fed. Rep. of Germany | 424/172 |
|---|---|---|---|
| 2306311 | 8/1973 | Fed. Rep. of Germany | 424/358 |
| 2807607 | 8/1978 | Fed. Rep. of Germany | 424/172 |
| 2033191 | 4/1970 | France | 424/358 |
| 4616118 | of 1971 | Japan | 424/39 |

OTHER PUBLICATIONS

Todd, Amer. Perf. & Cosmetics, 10/1971, vol. 86, pp. 112 to 115.
Todd, Cosmetics & Toiletries, 1/1976, vol. 91, pp. 29 to 32.
Schmolka, Amer. Perf. & Cosmetics, 7/1967, pp. 25–30.

*Primary Examiner*—Dale R. Ore
*Attorney, Agent, or Firm*—George A. Grindahl

[57] ABSTRACT

Antiperspirant emulsion compositions are described which comprise an aqueous solution of an astringent agent; a volatile, water-insoluble liquid; a polydiorganosiloxane-polyoxyalkylene copolymer; an oil-in-water type surfactant; and a water-in-oil type surfactant. A preferred embodiment comprises an emulsion of aqueous aluminum chlorhydrate in cyclopolydimethylsiloxanes as the volatile fluid. These compositions have improved efficacy as measured by their drying times.

4 Claims, No Drawings

ANTIPERSPIRANT EMULSION COMPOSITIONS

BACKGROUND OF THE INVENTION

This invention relates to antiperspirant compositions of the so-called dry-feeling type, comprising an emulsion of an aqueous solution of an astringent in a volatile, water-insoluble liquid and having improved efficacy.

Antiperspirant compositions are well known in the cosmetic art. These compositions are formulated as aerosols, gels, sticks, creams, pump sprays and lotions and comprise an astringent, typically comprising one or more zirconium salts and/or aluminum salts, in various forms such as a dry, impalpable powder, an alcohol solution or an aqueous solution. Of these various forms of astringents the aqueous solution is known to be the most effective antiperspirant.

However, an antiperspirant composition having water as the continuous phase, such as an aqueous solution of an astringent, or an oil-in-water type emulsion thereof, is less desirable than a composition comprising a dry powder or an alcohol solution thereof because it tends to feel wet when applied to the human skin and to go through a tacky state during the drying period after application.

Gee et al., U.S. Pat. No. 4,122,029 have disclosed water-in-oil type compositions having broad utility and comprising a polydiorganosiloxane-polyoxyalkylene copolymer and a water-in-oil type surfactant. When formulated as an antiperspirant emulsion of an aqueous solution of an astringent, such as aluminum chlorhydrate, emulsified in a volatile, non-aqueous continuous phase the compositions of Gee et al. have a desirable dry feeling when applied to the human skin and do not exhibit the wet-and-tacky effect noted above. However, said antiperspirant emulsions lack the full efficacy of aqueous or oil-in-water type antiperspirant compositions.

SUMMARY OF THE INVENTION

It is an object of this invention to provide antiperspirant emulsion compositions of the water-in-oil type which have improved efficacy. It is a further object of this invention to provide improved antiperserpirant compositions comprising an emulsion of aqueous aluminum chlorhydrate in a volatile silicone fluid.

The present invention achieves these objects, and others which will be obvious upon consideration of this disclosure, by adding an oil-in-water type surfactant to the antiperspirant compositions of Gee et al. Surprisingly, the resulting compositions comprising a water-in-oil type surfactant and an oil-in-water type surfactant are not only stable but they exhibit improved efficacy and still exhibit the dry feeling.

While not wishing to be limited by theory I believe that the antiperspirant compositions of Gee et al. exhibit less-than-expected efficacy because the astringent becomes temporarily and/or partially unavailable by encapsulation in a water-insoluble component of the formulation and that inclusion of an oil-in-water type surfactant decreases this action.

DETAILED DESCRIPTION OF THE INVENTION

This invention relates to an improved antiperspirant emulsion composition consisting essentially of (a) 30 to 60 parts by weight of an aqueous solution of an astringent as a discontinuous phase, (b) 27 to 67.5 parts by weight of a volatile liquid having a normal boiling point of less than 250° C. as a continuous phase, said volatile liquid being selected from the group consisting of methylsiloxane fluids having the average unit formula $$(CH_3)_a SiO_{(4-a)/2}$$

wherein a has an average value of from 2 to 3 inclusive, and paraffinic hydrocarbon fluids, (c) 0.5 to 3 parts by weight of an organic water-in-oil type surfactant having an HLB value of from 2 to 10, inclusive, (d) 1 to 5 parts by weight of a polydiorganosiloxane-polyoxyalkylene copolymer containing at least one polydiorganosiloxane segment consisting essentially of $R_b SiO_{(4-b)/2}$ siloxane units wherein b has a value of from 0 to 3, inclusive, there being an average value of approximately 2 R radicals per silicon for all siloxane units in the copolymer, and R denotes a radical selected from the group consisting of methyl, ethyl, vinyl, phenyl and a divalent radical bonding a polyoxyalkylene segment to the polydiorganosiloxane segment, at least 95 percent of all R radicals being methyl; and at least one polyoxyalkylene segment having an average molecular weight of at least 1000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisified by a terminating radical; the weight ratio of polydiorganosiloxane segments to polyoxyalkylene segments in said copolymer having a value of from 2 to 8, and (e) 1 to 5 parts by weight of an organic oil-in-water type surfactant having an HLB value of from 11 to 17, inclusive, the total of (a) plus (b) plus (c) plus (d) plus (e) being 100 parts by weight.

Component (a) is an aqueous solution of any astringent antiperspirant agent. Examples of well-known astringents include the aluminum, hafnium and zirconium salts, such as zirconyl hydroxide halides, zirconium-aluminum complex salts, aluminum chloride, sodium aluminum lactate, basic aluminum halides such as $Al_2(OH)_5Cl$, aluminum bromide and the several water, alcohol or glycine complexes thereof.

The amount of astringent that is dissolved in water to form component (a) may vary widely and is not critical; however, certain practical limitations exist. On the one hand an efficacious antiperspirant composition should contain sufficient astringent to provide sweat reduction, although compositions containing less astringent are useful as personal care compositions. Preferably the antiperspirant composition comprises approximately 15–30 weight percent astringent. On the other hand it is desirable to maximize the amount of water in the antiperspirant formulation without negating utility, for obvious economic reasons. Depending on the particular astringent that is used, component (a) may vary in concentration from as little as one part by weight astringent per three parts by weight water up to a saturated aqueous solution of the astringent. Considering economy and efficacy, a particularly useful component (a) is an aqueous solution of aluminum chlorhydrate consisting of equal weight portions of water and aluminum chlorhydrate.

The volatile liquid (b) is a fluid selected from the group consisting of methylsiloxane fluids, paraffinic hydrocarbon fluids and their mixtures, further detailed below. To be suitable as a volatile fluid for an antiperspirant composition component (b) should have a normal, i.e. atmospheric pressure, boiling point of less than 250° C. Methylsiloxane fluids and paraffinic hydrocarbon fluids meeting this parameter also typically have a viscosity at 25° C. of less than 10 millipascal-seconds (mPa.s). One millipascal-second equals one centipose. To avoid an excessive cooling effect for the user of the compositions of this invention it is preferred that at least a portion of the volatile liquid have a normal boiling point of from 100° to 200° C.

The volatile methylsiloxane fluid (b) has the average unit formula $$(CH_3)_a SiO_{(4-a)/2}$$

where a has an average value of from 2 to 3 and consists of siloxane units selected from the group consisting of $(CH_3)_3SiO_{\frac{1}{2}}$, $(CH_3)_2SiO_{2/2}$, $CH_3SiO_{3/2}$ and $SiO_{4/2}$ units. Preferably the volatile methylsiloxane fluid consists essentially of dimethylsiloxane units, and optionally, trimethylsiloxane units. Of particular value as volatile liquid (b) are the cyclic siloxanes of the general formula $\{(CH_3)_2SiO\}_x$ and the linear siloxanes of the general formula $(CH_3)_3SiO\{(CH_3)_2SiO\}_y Si(CH_3)_3$, and their mixtures, wherein x is an integer of from 3 to 6 and y is an integer of from 0 to 4. A highly preferred methylsiloxane fluid is a mixture of said cyclic siloxanes wherein a major portion is tetramer (x=4).

Paraffinic hydrocarbon fluids suitable for use as component (b) in these compositions correspond to the average unit formula $C_nH_{2n+2}$, in the well-known manner, wherein n is an integer having a value of less than 15. A particularly suitable paraffinic hydrocarbon fluid is a high-purity isoparaffin available from Exxon Corporation as Isopar ™. Gaseous paraffins are typically used under super-atmospheric pressure, such as in an aerosol formulation, to keep them in the liquid state.

The volatile fluid, in addition to being a methylsiloxane fluid or a paraffinic hydrocarbon fluid, may be any mixture of said methylsiloxane fluid and said paraffinic fluid, such as a mixture of octamethylcyclotetrasiloxane and hexane or decamethylcyclopentasiloxane and butane or a mixture of two or more of said cyclosiloxanes and one or more paraffins. The emulsion compositions of this invention are stable to further dilution with a paraffinic hydrocarbon. This is of particular advantage in the preparation of antiperspirant emulsions which will not break when formulated as a spray-can composition using a gaseous paraffin, such as isobutane, as the propellant.

Methylsiloxane fluids and parraffinic hydrocarbons, suitable for use as volatile fluid (b) in the compositions of this invention, are well known in the chemical and polymer arts; many are commercially available.

Component (c) is any cationic or nonionic organic surfactant suitable for preparing emulsions of the water-in-oil type and having an HLB (hydrophilic-lipophilic balance) value of from 2 to 10, inclusive. Examples of suitable water-in-oil type surfactants include quaternary ammonium chlorides supplied by Tomah Products, Inc. as Emulsifier Three ™ and Emulsifier Four ™ as a cationic surfactant and polyethylene glycol (200) monolaurate, glycerol monolaurate, N,N-dimethylcaproamide, diethylene glycol monolaurate, sorbitan monolaurate and nonylphenoxy polyethoxyethanol as nonionic surfactants. Mixtures of cationic and/or nonionic water-in-oil surfactants are also suitable. Other examples of suitable organic surfactants having an HLB value of from 2 to 10 may be found by consulting standard surfactant publications such as McCutcheon's "Detergents and Emulsifiers" 1975 North American Edition, MC Publishing Company, Glen Rock, NJ 1975.

Component (d) is a polydiorganosiloxanepolyoxyalkylene copolymer containing at least one polydiorganosiloxane segment and at least one polyoxyalkylene segment. The polyoxyalkylene segments may be bonded to the polydiorganosiloxane segments with silicon-oxygen-carbon bonds and/or with silicon-carbon bonds. Although component (d) is not soluble in water and is therefore not subjected to vigorous hydrolysis in the compositions of this invention, it is preferred that the copolymer (d) have silicon-carbon bonding instead of the more hydrolyzable silicon-oxygen-carbon bonding joining the polyoxyalkylene segments to the polydiorganosiloxane segments.

The polydiorganosiloxane segments of the copolymer (d) consist essentially of siloxane units which are interlinked by Si-O-Si linkages and which have the formula $$R_b SiO_{(4-b)/2}.$$

The value of b may range from 0 to 3 for said siloxane units with the provision that there is an average of approximately 2, i.e. from 1.9 to 2.1 R radicals for every silicon in the copolymer. Suitable siloxane units thus include $R_3SiO_{\frac{1}{2}}$, $R_2SiO_{2/2}$, $RSiO_{3/2}$, and $SiO_{4/2}$ siloxane units taken in such molar amounts so that b has an average value of approximately 2 in the copolymer. Said siloxane units may be arranged in linear, cyclic and/or branched fashion.

The R radicals of copolymer (d) may be any radical selected from the group consisting of methyl, ethyl, vinyl, phenyl, and a divalent radical bonding a polyoxyalkylene segment to the polydiorganosiloxane segment. At least 95 percent of all R radicals in the copolymer (d) are methyl radicals; preferably there is at least one methyl radical bonded to each silicon atom in (d). Divalent R radicals preferably contain no more than 6 carbon atoms. Examples of divalent R radicals include $-O-$, $-C_mH_{2m}O-$, $-C_mH_{2m}-$ and $-C_mH_{2m}CO_2-$ where m is an integer greater than zero.

Illustrative of the siloxane units that make up the polydiorganosiloxane segments of the copolymer (d) are the following, where Me denotes methyl and Q denotes said divalent R radical and bonded polyoxyalkylene segment: $R_3SiO_{\frac{1}{2}}$ units such as $Me_3SiO_{\frac{1}{2}}$, $Me_2(CH_2=CH)SiO_{\frac{1}{2}}$, $Me_2(C_6H_5)SiO_{\frac{1}{2}}$, $Me(C_6H_5)(CH_2=CH)SiO_{\frac{1}{2}}$, $Me_2(CH_3CH_2)SiO_{\frac{1}{2}}$, $Me_2QSiO_{\frac{1}{2}}$, $MeQ_2SiO_{\frac{1}{2}}$, $Q_3SiO_{\frac{1}{2}}$, $Q_2(CH_3CH_2)SiO_{\frac{1}{2}}$, and $Me(C_6H_5)(Q)SiO_{\frac{1}{2}}$; $R_2SiO_{2/2}$ units such as $Me_2SiO_{2/2}$, $Me(C_6H_5)SiO_{2/2}$, $Me(CH_2=CH)SiO_{2/2}$, $(C_6H_5)_2SiO_{2/2}$, $MeQSiO_{2/2}$, and $Q(C_6H_5)SiO_{2/2}$; $RSiO_{3/2}$ units such as $MeSiO_{3/2}$, $C_6H_5SiO_{3/2}$, $CH_2=CHSiO_{3/2}$, $CH_3CH_2SiO_{3/2}$ and $QSiO_{3/2}$; and $SiO_{4/2}$ units.

It is to be understood that copolymer (d) may comprise one or more of said polydiorganosiloxane segments. The number of and average molecular weight of the polydiorganosiloxane segments in the copolymer is related to the desired weight ratio, hereinafter described, of said segments in the copolymer. Preferably copolymer (d) comprises on polydiorganosiloxane segment having bonded thereto one or more polyoxyalkylene segments.

The polyoxyalkylene segments of the copolymer (d) consist essentially of oxyethylene units of the formula —$CH_2CH_2O$—, alone, or in combination with oxypropylene units of the formula —$CH_2CH(CH_3)O$—, an average of at least half of the oxyalkylene units in the polyoxyalkylene segments being oxyethylene units. Suitable emulsions of this invention are not formed when the polyoxyalkylene segments contain more than 50 mol percent of the relatively hydrophobic oxypropylene unit. The polyoxyalkylene segments thus correspond to the formula $\{$—$CH_2CH_2O$—$\}_p$-$\{$—$CH_2CH(CH_3)O$—$\}_q$ wherein the oxyalkylene units may be arranged in any suitable fashion such as random, alternating and block. The average values of p and q are such that $p \geq q$ and the sum of $p+q$ is sufficient to provide an average molecular weight of at least 1,000 for the polyoxyalkylene segments. Preferably the average molecular weight of the polyoxyalkylene segments has a value of from 1,500 to 5,000.

The polyoxyalkylene segments of the copolymer (d) are bonded to the polydiorganosiloxane segments of said copolymer by at least one terminal portion of said polyoxyalkylene segment, said bonding being by way of a divalent R radical, hereinbefore described. It is to be understood that said bonding may be by both terminal portions of said polyoxyalkylene segment in those copolymers comprising more than one polydiorganosiloxane segments. Any terminal portion of the polyoxyalkylene segment of copolymer (d) that is not bonded to a polydiorganosiloxane segment is satisfied by a terminating radical. The type of said terminating radical is not critical and may be monovalent, thereby terminating one polyoxyalkylene segment, or polyvalent, thereby terminating more than one polyoxyalkylene segment. Said terminating radicals are made up of atoms selected from the group consisting of carbon, hydrogen, nitrogen, and oxygen. Illustrative of said terminating radical are hydrogen; hydroxyl; alkyl, such as methyl, ethyl, propyl, butyl; benzyl; aryl, such as phenyl; alkoxy such as methoxy, ethoxy, propoxy, butoxy; benzyloxy; aryloxy, such as phenoxy; alkenyloxy, such as vinyloxy and allyloxy; acyloxy, such as acetoxy, acryloxy and propionoxy and amino such as dimethylamino.

The number of and average molecular weights of the segments in the copolymer (d) are such that the weight ratio of polydiorganosiloxane segments to polyoxyalkylene segments in copolymer (d) has a value of from 2 to 8, and preferably from 2.5 to 4.0. This weight ratio will insure that the copolymer (d) has a preferential solubility in the volatile liquid, a condition necessary for the formation of stable water-in-oil type emulsions of this invention.

The weight ratio of polydiorganosiloxane segments to polyoxyalkylene segments in copolymer (d) is calculated on the basis of the total weight of polydiorganosiloxane and the total weight of polyoxyalkylene that is joined in the copolymerization process. For example, if 100 parts by weight of polydiorganosiloxane is joined completely by an addition process, which utilizes silicon-bonded hydrogen radicals, with 20 parts by weight of polyoxyalkylene, said weight ratio of the resulting copolymer has a value of 5. Of course, if said complete joining is accomplished by a displacement reaction, involving a silicon-bonded hydrolyzable radical and resulting in the formation of a by-product, the weight ratio of polydiorganosiloxane to polyoxyalkylene in the resulting copolymer may not be identical with the weight ratio of the corresponding reactants, due to the loss of the weight of the displaced groups. The error introduced into the calculation of said weight ratio by ignoring the loss of said displaced groups is usually insignificant. That is to say, the weight ratio of polydiorganosiloxane to polyoxyalkylene in copolymer (d) may be calculated from the weight of reactants that react to form the copolymer or said weight ratio may be determined by suitable analysis of the resulting copolymer itself. Suitable analytical techniques such as elemental analysis, nuclear magnetic resonance spectroscopy, silicon substituent analysis and infra-red spectroscopy may be found in "Analysis of Silicones", A. Lee Smith, Ed., John Wiley and Sons, New York, 1974.

Herein, copolymer means either a block arrangement of segments such as denoted by the formulae $(AB)_c$, $A(BA)_c$ and $B(AB)_c$ or a pendant arrangement of segments such as $(AB_d)_c$ or combinations thereof wherein A denotes a polydiorganosiloxane segment, B denotes a polyoxyalkylene segment and c and d denote integers greater than zero and greater than one, respectively.

Copolymers (d) may be prepared by modifications of the well-known methods described in the polydiorganosiloxane-polyoxyalkylene copolymer art. The following patents are hereby incorporated by reference to show the preparation of polydiorganosiloxane-polyoxyalkylene copolymers: Haluska, U.S. Pat. No. 2,868,824; Haluska, U.S. Pat. No. Re 25,727; Bailey, U.S. Pat. No. 3,172,899; Pater, U.S. Pat. No. 3,234,252, Simmler, et al. U.S. Pat. No. 3,174,987; Bailey, et al., U.S. Pat. Nos. 3,562,786, 3,600,418 and 3,629,308; Holdstock, U.S. Pat. No. 3,629,165; and Gee et al., U.S. Pat. No. 4,122,029.

It is to be understood that the silicon-bonded reaction groups such as silicon-bonded hydrogen for addition reactions or silicon-bonded hydrolyzable radicals for displacement reactions are preferably completely reacted in the copolymer preparation process, but that trace amounts of said reaction groups may escape reaction with the polyoxyalkylene and may be found in the copolymer (d).

Component (e) is any cationic or nonionic organic surfactant being suitable for preparing emulsions of the oil-in-water type and having an HLB value of from 11 to 17, inclusive. Examples of oil-in-water type surfactants include polyethoxylated quaternary ammonium salts and polyoxyethylene fatty amines as cationic surfactants, and polyethylene-glycol alkylethers, polyethyleneglycol alkylarylethers, polyethoxylated sorbitan monolaurate, polyoxyethylene lanolin derivatives and polyethoxylated fatty alcohols as nonionic surfactants. Mixtures of cationic and/or nonionic oil-in-water surfactants are also suitable. Other examples of suitable organic surfactants having an HLB value of from 11 to 17 may be found by consulting standard publications such as McCutcheon's "Detergents and Emulsifiers", 1975 North America Edition, MC Publishing Co., Glen Rock, NJ 1975.

The amounts of components (a) and (b) that may be present in the compositions of this invention may vary widely and comprises, in total, from 87 to 97.5 percent by weight of the total weight of components (a) through (e). The aqueous solution (a) of astringent may comprise from 30 to 60, preferably 40 to 50, weight percent of components (a) through (e); however, as noted above, an efficacious antiperspirant should contain a sweat-reducing amount, preferably from 15 to 30 percent by weight, of the astringent agent itself. A preferred embodiment of this invention is a composition comprising from 30 to 60 percent by weight of an aqueous solution of astringent which consists of approximately 50 weight percent portions of water and the astringent. The volatile liquid (b) comprises from 27 to 67.5 weight percent of the total weight of components (a) to (e).

The surfactant mixture, consisting essentially of components (c), (d) and (e), comprises, in total, from 2.5 to 13 percent by weight of the total weight of components (a) to (e), with component (c) accounting for from 0.5 to 3 weight percent, component (d) accounting for from 1 to 5 weight percent and component (e) accounting for from 1 to 5 weight percent of the total of components (a) to (e).

The compositions of this invention may further comprise small amounts of non-essential components which are used in the cosmetic art. Examples of such components include colorants; perfumes; viscosity control additives, such as solvents or thickening agents for the continuous phase; and non-volatile organopolysiloxanes, such as polydimethylsiloxanes having a viscosity of from 10 to 10,000 millipascal-seconds at 25° C.

The compositions of this invention are suitable for use, without further processing, as a lotion, preferably packaged and dispersed as a roll-on antiperspirant composition. However, gel, aerosol and pump-spray formulations may be prepared therefrom using well-known adjuvants such as alcohols for gel-formation and solvents to reduce the viscosity of the formulation to less than 100 millipascal-seconds at 25° C. for aerosol and pump-spray use. My copending application, "Antiperspirant Stick Compositions", filed on even data herewith and assigned to the assignee of this application, discloses novel compositions and methods which are useful for preparing stick compositions from the improved compositions of this invention.

The compositions of this invention may be prepared by mixing the proper portions of the individual components in any order. Although the compositions of this invention are delineated in terms of an aqueous solution of an astringent (a) emulsified in a volatile liquid (b) using a mixture of surfactants, (c), (d), and (e), the following examples show that said compositions are preferably prepared by preparing a so-called aqueous phase comprising the aqueous solution of an astringent (a) and the oil-in-water type surfactant (e) and preparing a so-called oily phase comprising the volatile liquid (b), the water-in-oil type surfactant (c) and the polydiorganosiloxane-polyoxyalkylene copolymer (d) and thereafter mixing the so-called aqueous phase with the so-called oily phase. Mixing may be done using standard emulsifying methods.

Now in order that those skilled in the art may better understand how the present invention can be practiced, the following specific components and examples are disclosed for purposes of illustrating and not limiting the invention. All percentages and parts are by weight, all viscosities were measured in centipoise at 25° C. and were converted to millipascal-seconds (mPa·s) by multiplying by 1.000 millipascal-second/centipoise and all pressures were measured in millimeters of mercury and were converted to kilopascals by multiplying by 0.1333224 and rounding off.

Polydiorganosiloxane-polyoxyalkylene Copolymer

The polydiorganosiloxane-polyoxyalkylene copolymer that was used in the following examples, and designated as "Copolymer" in Tables II to V, was prepared from a trimethylsiloxane-endblocked polydimethylsiloxane having a molecular weight of approximately 30,000 and having an average of approximately 4 of its dimethylsiloxane units replaced with methylhydrogensiloxane units, and a random equimolar polyglycol copolymer of ethylene oxide and propylene oxide having an average molecular weight of approximately 2550 and having allyloxy endgroups on one end and acetoxy endgroups on the other end. Two hundred twenty grams of the siloxane, 80.76 grams of the polyglycol and 75.19 grams of isopropanol were mixed and heated to reflux under dry nitrogen in a flask and the resulting solution was catalyzed with 0.15 ml. of a 1 molar solution of $H_2PtCl_6$ in isopropanol. The reaction mixture was heated at reflux for one hour and then devolatilized at 110° C. and 1.33 kilopascals pressure. The polydimethylsiloxane-polyoxy alkylene copolymer product had a siloxane/oxyalkylene weight ratio of approximately 2.7 and —$CH_2CH_2CH_2O$— divalent radicals bonding the polyoxyalkylene portion to the polydimethylsiloxane portion by way of a silicon-carbon bond.

Surfactants

The water-in-oil surfactants and the oil-in-water surfactants that were used in the following examples are listed in Table I and are designated w/o (Item) and o/w (Item), respectively, in Tables II to V.

Volatile Liquid

The volatile liquid that was used in the following examples and designated as "Volatile Liquid" in Tables II to V was a commercially available mixture of a major amount of octamethylcyclotetrasiloxane and minor amounts of larger cyclic dimethylsiloxanes.

50% ACH

The antiperspirant astringent ingredient that was used in the following examples, and designated "50% ACH" in Tables II to V, was a 50 percent by weight solution of aluminum chlorhydrate in water.

Aqueous Phase

The aqueous phase noted in Tables II to V was prepared by dissolving the indicated oil-in-water surfactant in the 50 percent aqueous solution of aluminum chlorhydrate in the indicated proportions.

Oily Phase

The oily phase noted in Tables II to V was prepared by dissolving 1 part of the polydiorganosiloxane-polyoxyalkylene copolymer in 9 parts of the volatile liquid mixture of cyclic polydimethylsiloxanes to form a stock solution. A sufficient amount of this stock solution to provide the indicated amount of copolymer was then mixed with sufficient additional volatile liquid and the indicated amount and type of water-in-oil surfactant to provide the oily phase having the various compositions shown in the Tables.

Compositions

The compositions of this invention (Nos. 2 to 20 in Tables II to V) and the prior art control composition (No. 1 in Table II) were prepared by slowly adding the aqueous phase to the oily phase, in the indicated proportions, while the latter was being agitated in an Eppenbach brand homogenizer to provide the indicated compositions. The resulting emulsions were stable at 100° F.

for from 2 weeks to several months and were also stable after two freeze-thaw cycles.

Efficacy

Efficacy was measured by rolling the antiperspirant composition onto the palmar side of the wrist and noting the time required for the applied composition to begin to dry and turn white. An efficacy rating of less than 60 seconds in this test is highly desirable. Antiperspirant compositions having a rating of less than 60 seconds in this test have been found to have excellent efficacy for sweat reduction.

percent of an oil-in-water surfactant efficacy is greatly improved. Another comparison with the control composition is provided in Example 4. Composition No. 5 is discussed further in Example 2.

TABLE II

| Composition Number | Component - Parts | | | | | Antiperspirant Properties | |
|---|---|---|---|---|---|---|---|
| | Oily Phase | | | Aqueous Phase | | Viscosity- mPa . s | Efficacy- sec. |
| | Copolymer | Volatile Liquid | w/o (Item)* | 50% ACH | o/w (Item)* | | |
| 1** | 3.35 | 50.15 | 1.5(B) | 45.0 | None | 290 | 390 |
| 2 | 2.85 | 45.65 | 1.5(B) | 45.0 | 5.0 (L) | 240 | 25 |
| 3 | " | " | " | " | 5.0 (M) | 170 | 25 |
| 4 | " | " | " | " | 5.0 (N) | 180 | 40 |
| 5 | " | " | " | " | 5.0 (P) | 440 | 145 |
| 6 | " | " | " | " | 5.0 (Q) | 150 | 35 |

*See Table I for Item identity and HLB values for w/o and o/w surfactants
**Prior art composition; for comparison purposes only.

TABLE I

| | Water-in-Oil Surfactant | | | |
|---|---|---|---|---|
| Item | Trade Name | Supplier | Identity | HLB |
| A | Hodag 22L | Hodag Chem. Corp. | Polyethyleneglycol 200 dilaurate | 6.6 |
| B | Nonionic E-4 | Hodag Chem. Corp. | Polyoxyethylene alkylarylether | 8.6 |
| C | Pegosperse 200 ML | Glycol Chem. Inc. | Polyethyleneglycol 200 monolaurate | 8.6 |
| D | Witconal 14 | Witco Chem. Corp. | Polyglycerol fatty acid ester | — |
| | Oil-in-Water Surfactant | | | |
| Item | Trade Name | Supplier | Identity | HLB |
| L | Tergitol 15S9 | Union Carbide Corp. | Polyethyleneglycol alkylether | 13.3 |
| M | Nonionic E-12 | Hodag Chem. Corp. | Polyoxyethylene alkylarylether | 14.2 |
| N | Tergitol 15S15 | Union Carbide Corp. | Polyethyleneglycol alkylether | 15.4 |
| P | Tween 20 | ICI, America, Inc. | Ethylene oxide sorbitan monolaurate | 16.7 |
| Q | Nonionic E-20 | Hodag Chem. Corp. | Polyoxyethylene alkylarylether | 17.0 |

Source: "McCutcheon's Detergents and Emulsifiers", 1975 North American Edition McCutcheon Division, MC Publishing Co., Glen Rock, N.J., 1975, pp. 17-30.

EXAMPLE 2

This example demonstrates further improvement in efficacy of Composition No. 5 when the type and concentration of the water-in-oil surfactant is varied and the type and concentration of oil-in-water surfactant is held constant. (Compositions 7 to 11; Table III). Note that the viscosity of the antiperspirant is also controllable by this variation in composition.

TABLE III

| Composition Number | Component - Parts | | | | | Antiperspirant Properties | |
|---|---|---|---|---|---|---|---|
| | Oily Phase | | | Aqueous Phase | | Viscosity- mPa . s | Efficacy- sec. |
| | Copolymer | Volatile Liquid | w/o (Item)* | 50% ACH | o/w (Item)* | | |
| 5 | 2.85 | 45.65 | 1.5 (B) | 45.0 | 5.0 (P) | 440 | 145 |
| 7 | 2.90 | 46.10 | 1.0 (B) | " | " | 110 | 85 |
| 8 | 2.95 | 46.55 | 0.5 (B) | " | " | 90 | 55 |
| 9 | 2.85 | 45.65 | 1.5 (A) | " | " | 90 | 60 |
| 10 | " | " | 1.5 (C) | " | " | 100 | 65 |
| 11 | " | " | 1.5 (D) | " | " | 150 | 25 |

*See Table I for Item identity and HLB values for w/o and o/w surfactants.

EXAMPLE 1

This example demonstrates the improvement in efficacy of the antiperspirant compositions of this invention having 5 percent of various oil-in-water surfactants (Compositions 2 to 6, Table II) compared with a prior art antiperspirant composition having no oil-in-water surfactant (Composition 1, Table II). Note that when 5 percent of the 1:9 stock solution of copolymer in volatile liquid in the prior art composition is replaced with 5

EXAMPLE 3

This example demonstrates the viscosity and efficacy values that are available in a composition of this invention as the aqueous phase concentration is varied from 45 to 55 percent of the composition (Compositions 12, 14 and 7; Table IV) or as the water-in-oil surfactant concentration is varied from 0.5 to 1.5 percent of the composition (Compositions 13, 14 and 15; Table IV).

TABLE IV

| Composition Number | Component - Parts | | | | | Antiperspirant Properties | |
|---|---|---|---|---|---|---|---|
| | Oily Phase | | | Aqueous Phase | | Viscosity- | Efficacy- |
| | Copolymer | Volatile Liquid | w/o (Item)* | 50% ACH | o/w (Item)* | mPa . s | sec. |
| 12 | 2.35 | 36.65 | 1.0 (B) | 55 | 5 (P) | 490 | 55 |
| 13 | 2.35 | 41.15 | 1.5 (B) | 50 | " | 300 | 45 |
| 14 | 2.35 | 41.65 | 1.0 (B) | 50 | " | 150 | 35 |
| 15 | 2.35 | 42.15 | 0.5 (B) | 50 | " | 110 | 35 |
| 7 | 2.90 | 46.10 | 1.0 (B) | 45 | " | 110 | 85 |

*See Table I for Item identity and HLB values for w/o and o/w surfactants.

EXAMPLE 4

This example provides a comparison of a prior art composition and a composition of this invention (Compositions No. 1 and 20; Table V). In this case the oily phases of each composition are identical and a portion of the 50% ACH component is replaced with the oil-in-water type surfactant. Other compositions of this invention which comprise the same o/w and w/o surfactants are also disclosed (Compositions 2, 16-19). All compositions of this invention possess excellent efficacy.

TABLE V

| Composition Number | Component - Parts | | | | | Antiperspirant Properties | |
|---|---|---|---|---|---|---|---|
| | Oily Phase | | | Aqueous Phase | | Viscosity- | Efficacy- |
| | Copolymer | Volatile Liquid | w/o (Item)* | 50% ACH | o/w (Item)* | mPa . s | sec. |
| 2 | 2.85 | 45.65 | 1.5 (B) | 45 | 5 (L) | 240 | 25 |
| 16 | 2.85 | 45.65 | " | 50 | " | 900 | 25 |
| 17 | 2.50 | 41.00 | " | " | " | 1100 | 20 |
| 18 | 2.35 | 41.15 | " | " | " | 680 | 30 |
| 19 | 2.35 | 38.65 | " | 52.5 | " | 1580 | 25 |
| 20 | 3.35 | 50.15 | " | 42.5 | 2.5 (L) | 970 | 40 |
| 1** | 3.35 | 50.15 | " | 45.0 | None | 290 | 390 |

*See Table I for Item identity and HLB values for w/o and o/w surfactants.
**Prior art composition; for comparison purposes only.

That which is claimed is:

1. A water-in-oil antiperspirant emulsion composition having improved efficacy consisting essentially of
   (a) 30 to 60 parts by weight of an aqueous solution of an astringent as a discontinuous phase,
   (b) 27 to 67.5 parts by weight of a volatile liquid having a normal boiling point of less than 250° C. as a continuous phase, said volatile liquid being selected from the group consisting of methylsiloxane fluids having the average unit formula $$(CH_3)_a SiO_{(4-a)/2}$$

wherein a has an average value of from 2 to 3, inclusive, and paraffinic hydrocarbon fluids,
   (c) 0.5 to 3 parts by weight of an organic water-in-oil surfactant having an HLB value of from 2 to 10, inclusive,
   (d) 1 to 5 parts by weight of a polydiorganosiloxane-polyoxyalkylene copolymer containing at least one polydiorganosiloxane segment and at least one polyoxyalkylene segment, said polydiorganosiloxane segment consisting essentially of $$R_b SiO_{(4-b)/2}$$

siloxane units wherein b has a value of from 0 to 3, inclusive, there being an average value of approximately 2 R radicals per silicon for all siloxane units in the copolymer, and R denotes a radical selected from the group consisting of methyl, ethyl, vinyl, phenyl and a divalent radical bonding said polyoxyalkylene segment to the polydiorganosiloxane segment, at least 95 percent of all R radicals being methyl; and said polyoxyalkylene segment having an average molecular weight of at least 1000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from 2 to 8, and
   (e) 1 to 5 parts by weight of an organic oil-in-water surfactant having an HLB value of from 11 to 17, inclusive, the total of (a) plus (b) plus (c) plus (d) plus (e) being 100 parts by weight.

2. The antiperspirant emulsion composition of claim 1 wherein the water-in-oil surfactant and the oil-in-water surfactant are nonionic surfactants.

3. The antiperspirant emulsion composition of claim 1 or 2 wherein the volatile liquid is a mixture of cyclic dimethylsiloxanes consisting of octamethylcyclotetrasiloxane and larger cyclic dimethylsiloxanes.

4. The antiperspirant emulsion composition of claim 3 wherein the aqueous solution of an astringent antiperspirant agent consists of equal weights of water and aluminum chlorhydrate and comprises from 40 to 50 percent by weight of the total weight of components (a) to (e).

* * * * *

UNITED STATES PATENT AND TRADEMARK OFFICE
CERTIFICATE OF CORRECTION

PATENT NO. : 4,268,499

DATED : May 19, 1981

INVENTOR(S) : Joseph W. Keil

It is certified that error appears in the above-identified patent and that said Letters Patent are hereby corrected as shown below:

In Column 1, line 44; the word reading "antiperserpirant" should read "antiperspirant".

In Column 3, line 36; the name reading "Isopar TM" should read "Isopar$^{TM}$".

In Column 3, line 62; the name reading "Emulsifier Three TM" should read "Emulsifier Three$^{TM}$".

In Column 3, line 62; the name reading "Emulsifier Four TM" should read "Emulsifier Four$^{TM}$".

In Column 4, line 24; the formula reading "$R_b SiO_{(4\{b)/2}}$" should read "$R_b SiO_{(4-b)/2}$".

In Column 4, line 66; the word reading "on" should read "one".

UNITED STATES PATENT AND TRADEMARK OFFICE
CERTIFICATE OF CORRECTION

PATENT NO. : 4,268,499

DATED : May 19, 1981

INVENTOR(S) : Joseph W. Keil

It is certified that error appears in the above-identified patent and that said Letters Patent are hereby corrected as shown below:

In Column 7, line 32; the word reading "data" should read "date".

Signed and Sealed this

Twenty-ninth Day of September 1981

[SEAL]

Attest:

GERALD J. MOSSINGHOFF

Attesting Officer

Commissioner of Patents and Trademarks